United States Patent [19]
McCarthy et al.

[11] Patent Number: 5,343,818
[45] Date of Patent: Sep. 6, 1994

[54] PHOTOPLETHYSMOGRAPHICS USING ENERGY-REDUCING WAVEFORM SHAPING

[75] Inventors: Rex McCarthy, Newbury Park; Robert Smith, Corona, both of Calif.

[73] Assignee: Sensormedics Corp., Yorba Linda, Calif.

[21] Appl. No.: 664,782

[22] Filed: Mar. 5, 1991

[51] Int. Cl.$^5$ ............................................. A61B 5/00
[52] U.S. Cl. .................................. 128/633; 128/666; 364/413.03
[58] Field of Search ........................ 128/633, 664–666; 356/41; 250/343; 364/413.03

[56] References Cited

U.S. PATENT DOCUMENTS

| | | | |
|---|---|---|---|
| 4,800,885 | 1/1989 | Johnson | 128/633 |
| 4,807,630 | 2/1989 | Malinouskas | 128/633 |

*Primary Examiner*—Lee S. Cohen
*Assistant Examiner*—Robert L. Nasser, Jr.
*Attorney, Agent, or Firm*—Lyon & Lyon

[57] ABSTRACT

A method of energy-reducing waveform shaping of carrier signals in a photoplethysmographic system, in which a carrier signal may comprise a time-varying periodic waveform comprising a sum of carrier components. The carrier signal has its energy reduced by adding additional carrier components, which reduce the energy envelope for a period of the carrier signal, while preserving the signal information. The method of energy-reducing waveform shaping may be coupled with frequency-division, phase-division and component-amplitude-division multiplexing, and more generally with any method of multiplexing which employs a time-varying periodic carrier signal. Redundant information may be used for error detection and correction. A plurality of carrier components may be chosen which reduces the energy envelope for a period of the carrier signal, and which employs more carrier components than needed to perform the preferred form of multiplexing and demultiplexing of the modulation effects introduced by a tissue section of the patient. Majority voting of carrier components may then provide for error detection and correction.

51 Claims, 2 Drawing Sheets

PHOTOPLETHYSMOGRAPHICS USING ENERGY-REDUCING WAVEFORM SHAPING

BACKGROUND OF THE INVENTION

1. Field of the Invention

This invention relates to photoplethysmographics. More specifically, this invention relates to energy-reducing waveform shaping of signals to be applied to measure infrared and red absorption of blood.

2. Description of Related Art

It is well known in the art to collect photoplethysmographic data simultaneously at a plurality of energy wavelengths. For example, blood oxygen concentration may be measured by determining absorption by a patient's tissues on infrared and red light; the degree of absorption is typically different for these two wavelengths. Infrared and red light are emitted into the patient's tissues (e.g., by infrared and red LEDs) and the total energy received to be detected by a single detector (e.g., a photodiode). However, one problem is that the signal produced by the detector must be processed to separate the infrared and red portions from each other.

One method of the prior art is shown in U.S. Pat. No. 4,407,290. Time-division multiplexing is used to alternately switch on the infrared and red emitters, at a frequency greater than the patient's pulse rate. The detector signal is then separated into infrared and red portions by sampling in synchrony with the on/off switching of the infrared and red emitters.

While this method successfully separates the infrared and red portions, it generally requires that sampling the detector signal must be constantly synchronized with the on/off switching of the infrared and red emitters. It is also difficult while using this method to compensate for noise sources such as ambient light and electromagnetic interference.

A second method of the prior art is shown in U.S. Pat. No. 4,800,885. The infrared and red emitters are driven at two different frequencies. The detector signal is then separated into infrared and red portions by filtering at those two different frequencies.

While this method successfully separates the infrared and red portions, the method described in the patent requires demultiplexing signals which are phase-synchronized with the multiplexing frequencies, and produces a higher power output than the time-division multiplexing method. Also, while this method may avoid noise sources at predetermined and known frequencies, it is difficult to compensate for noise sources which were not known before the multiplexing frequencies were chosen.

SUMMARY OF THE INVENTION

The invention provides a method of energy-reducing waveform shaping of carrier signals in a photoplethysmographic system. A carrier signal may comprise a time-varying periodic waveform comprising a sum of carrier components (e.g., sine waves). The carrier signal has its energy reduced by adding additional carrier components, which reduce the energy envelope for a period of the carrier signal, while preserving the signal information. After modulation of the carrier by a tissue section of the patient, the added carrier components may be removed by filtering.

The invention may be combined with a preferred form of multiplexing and demultiplexing of the modulation effects introduced by a tissue section of the patient. Energy-reducing waveform shaping may be coupled with frequency-division, phase-division and component-amplitude-division multiplexing, and more generally with any method of multiplexing which employs a time-varying periodic carrier signal.

In a preferred embodiment, redundant information provided by the invention may be used for error detection and correction. A plurality of carrier components may be chosen which reduces the energy envelope for a period of the carrier signal, and which employs more carrier components than needed to perform the preferred form of multiplexing and demultiplexing of the modulation effects introduced by a tissue section of the patient. In a preferred embodiment, majority voting of carrier components may then provide for error detection and correction.

DESCRIPTION OF THE PREFERRED EMBODIMENT

An embodiment of this invention may be used together with inventions which are disclosed in a copending application titled "PHOTOPLETHYSMOGRAPHICS USING COMPONENT-AMPLITUDE-DIVISION MULTIPLEXING" application Ser. No. 07/665,594, filed the same day in the name of the same inventors, and a copending application titled "PHOTOPLETHYSMOGRAPHICS USING PHASE-DIVISION MULTIPLEXING", application Ser. No. 07/665,595, filed the same day in the name of the same inventors, both of which are hereby incorporated by reference as if fully set forth herein.

Photoplethysmographic System

Figure 1:
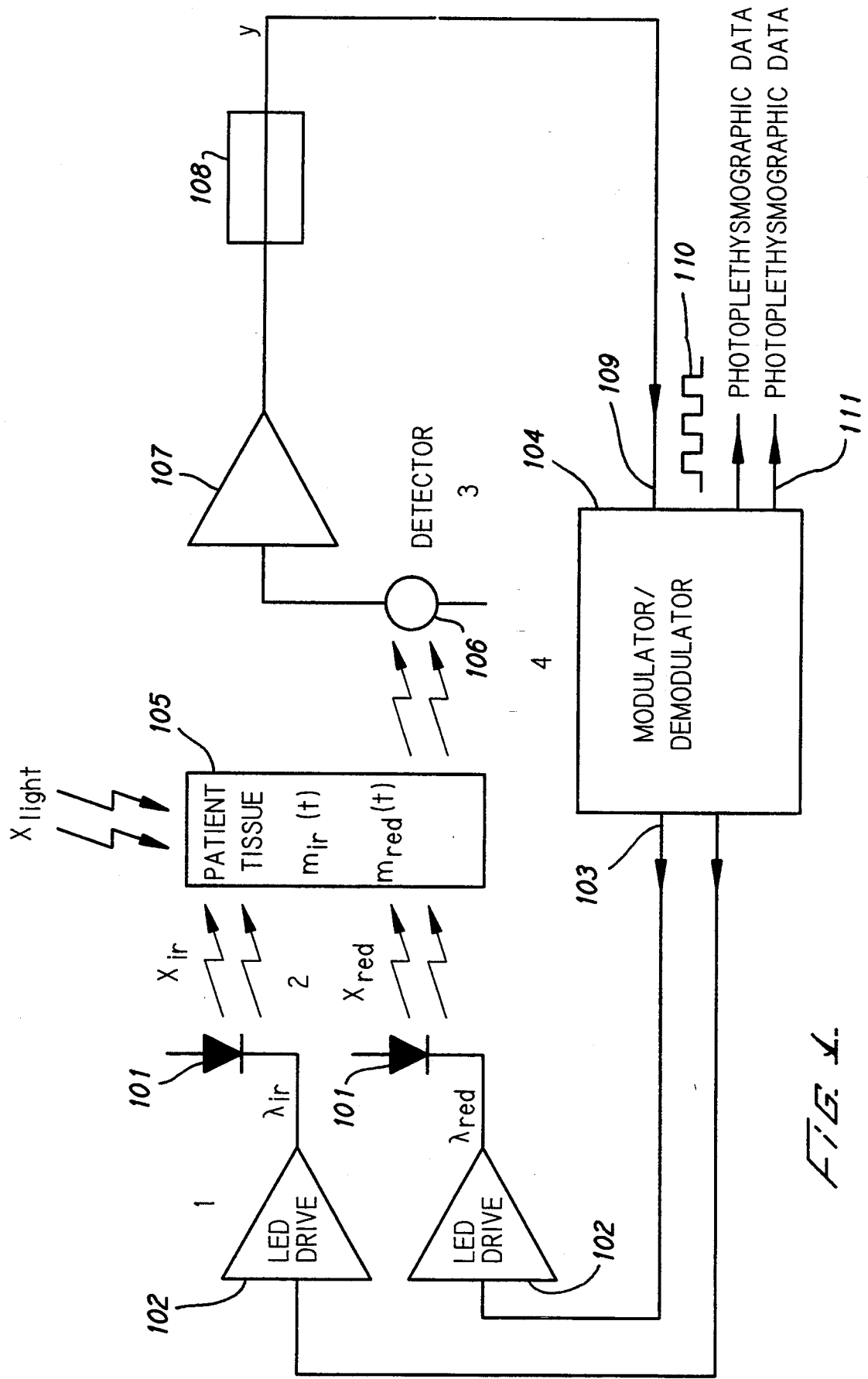
FIG. 1 shows a block diagram of a photoplethysmographic system comprising an embodiment of the invention.

FIG. 1 shows a block diagram of a photoplethysmographic system comprising an embodiment of the invention.

A plurality of energy emitters 101 may each be tuned to a separate wavelength. In a preferred embodiment for measuring blood oxygen, one of the emitters 101 may comprise an infrared emitter and may operate at a wavelength of about 880 nanometers; another one of the emitters 101 may comprise a red emitter and may operate at a wavelength of about 656 nanometers. However, it may occur that other wavelengths may be useful, such as for measuring blood carbon dioxide, blood carbon monoxide, other blood gas concentrations, blood glucose, or more generally, other chemical and/or physical concentrations.

Figure 2:
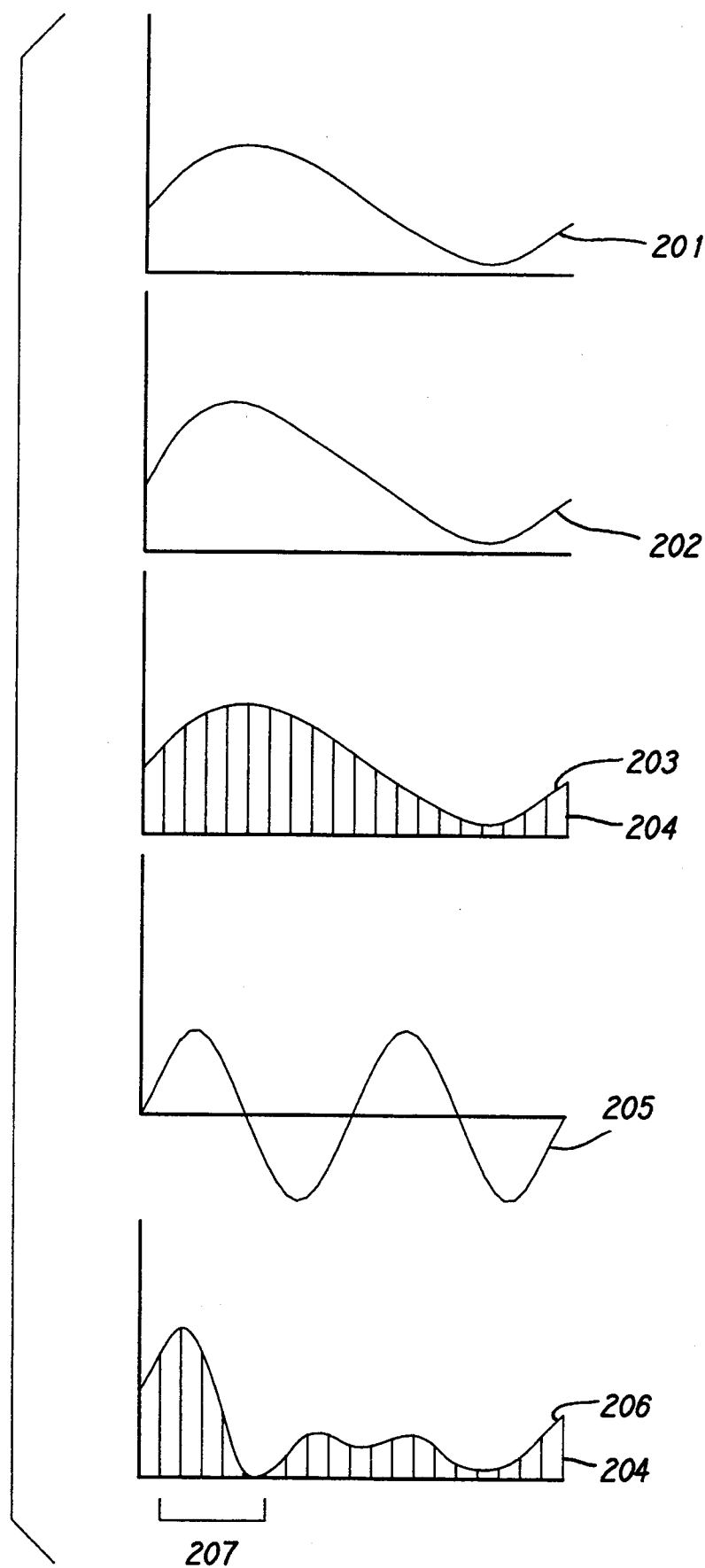
FIG. 2 shows some illustrative waveforms for signals used in an embodiment of the invention.

In a preferred embodiment, each of the emitters 101 may comprise an LED (such as part number OPC-8803 made by Marktech International Corp. for the infrared LED and part number MT1500-PUR made by Marktech International Corp. for the red LED), as is well known in the art, and may be coupled by means of an LED driver 102, as is well known in the art, to a carrier output 103 of a mux/demux circuit 104 (see FIG. 2).

Energy from the emitters 101 is applied to a tissue section 105 of a patient. In a preferred embodiment for measuring blood oxygen, the tissue section 105 is preferably chosen such that energy from the emitters 101 passes through the patient's blood vessels, such as an end of the patient's finger, the patient's earlobe, or (for neonates) the patient's hand or foot. The tissue section 105 may modulate the energy from the emitters 101, as is well known in the art, e.g., by absorbing some of the energy at each wavelength. Typically, energy may be modulated by transmission through the tissue section 105, but it may occur that energy may be modulated by reflection or by other means.

A detector 106 receives energy after modulation by the tissue section 105 and generates an output signal which indicates the total energy received. In a preferred embodiment, the detector 106 may comprise a photodiode (such as part number OSI-1140 made by Opto Sensors, Inc.) as is well known in the art. An output of the detector 106 is amplified by an amplifier 107 and coupled by means of a filter 108 to a detector input 109 of the mux/demux circuit 104.

The mux/demux circuit 104 generates a data output signal 110 at a data output 111, for each energy wavelength, which indicates the modulation which the tissue section 105 applied to that energy wavelength. In a preferred embodiment for measuring blood oxygen, information such as blood oxygen concentration may be calculated from the output signal, as is well known in the art.

Energy-Reducing Waveform shaping

FIG. 2 shows some illustrative waveforms for signals used in an embodiment of the invention.

As noted herein, energy-reducing waveform-shaping may be coupled with frequency-division, phase-division and component-amplitude-division multiplexing, and more generally with any method of multiplexing which employs a time-varying periodic carrier signal. The combination of the invention with these methods of multiplexing is disclosed herein. However, it would also be clear to one of ordinary skill in the art, after perusal of the specification, drawings and claims herein, how to combine the invention with each of these methods of multiplexing, and modification of each of these methods of multiplexing to incorporate the invention disclosed herein would thereafter be a straightforward task and would not require undue experimentation.

As noted herein, energy from the emitters 101 is applied to the tissue section 105 of a patient, according to the carrier output 103 of the mux/demux circuit 104. The carrier output may comprise a time-varying periodic carrier signal 201. The carrier signal 201 is modulated by the tissue section 105 of the patient by means of a plurality of modulation effects m1, m2, which are summed by the detector 106 and coupled to the detector input 109 of the mux/demux circuit 104. Measures of the modulation effects m1, m2 may be recovered from the detector input 109 by means of the method of multiplexing which the photoplethysmographic system employs.

The carrier signal 201 may comprise one or more periodic carrier components 202, which sum to produce a signal envelope 203. Energy from the emitters 101 is a function of an area under the curve 204 of the signal envelope 203. The area under the curve 204 may be reduced by adding a set of one or more additional carrier components 205 to the carrier signal 201, to produce an energy-reduced carrier signal 206. The energy-reduced carrier signal 206 comprises all the carrier components 202 which were present in the original carrier signal 201, plus the additional carrier components 205.

In a preferred embodiment, the carrier components 202 and the additional carrier components 205 are chosen such that interference from noise sources, such as ambient light and electromagnetic interference, is minimized. In a preferred embodiment, the carrier components 202 and the additional carrier components 205 are also chosen such that a bandwidth of about 4 Hz for the modulating effects m1, m2 is allowed. Frequencies in the range of about 10–50 Hz are preferred, but it would be clear to one of ordinary skill in the art, after perusal of the specification, drawings and claims herein, that other frequencies would be workable, and are within the scope and spirit of the invention.

In a preferred embodiment, the additional carrier components 205 are chosen to be harmonics which cause the total signal envelope 203 to approximate a 25% duty cycle waveform. In a preferred embodiment, those additional carrier components 205 which are nonzero components of a Fourier transform of a 25% duty cycle square wave may be used. However, it would be clear to one of ordinary skill in the art, after perusal of the specification, drawings and claims herein, that additional carrier components 205 chosen to match other signal envelopes would be workable, and are within the scope and spirit of the invention.

It would also be clear to one of ordinary skill in the art, after perusal of the specification, drawings and claims herein, that there is no requirement that the carrier components 202 and the additional carrier components 205 must be sine waves. Other types of carrier components 202, such as square waves or other waveforms, would be workable, and are within the scope and spirit of the invention.

Effect of Additional Carrier Components

The effect of the additional carrier components 205 on the photoplethysmographic system may depend on the method of multiplexing which the system employs.

One known method of multiplexing is frequency-division multiplexing, an embodiment of which is shown in U.S. Pat. No. 4,800,885. In frequency-division multiplexing, each carrier signal 201 has a carrier component 202 with a distinct frequency. The particular modulation effects m1, m2 are recovered by filtering the detector input 109 at each of those distinct frequencies in the mux/demux circuit 104.

In a system employing frequency-division multiplexing and energy-reduced carrier signals 206, the additional carrier components 205 will simply be filtered out by the mux/demux circuit 104, and thus have no adverse effect on demultiplexing.

Another method of multiplexing is component-amplitude-division multiplexing, an embodiment of which is shown in a copending application titled "PHOTOPLETHYSMOGRAPHICS USING COMPONENT-AMPLITUDE-DIVISION MULTIPLEXING", application Ser. No. 07/665,594, Lyon & Lyon Docket No. 190/193, filed the same day in the name of the same inventors, to which reference is made for explanation of that method of multiplexing. In component-amplitude-division multiplexing, each carrier signal 201 has the same plurality of carrier components 202, such that the carrier signals 201 all have the same period but are distinguishable by the amplitude of each carrier component 202 each carrier signal 201 comprises.

In a system employing component-amplitude-division multiplexing and energy-reduced carrier signals 206, the additional carrier components 205 have the same effect as in the $m>n>2$ case disclosed in that copending application, to which reference is made for explanation. Amplitudes must be selected for the additional carrier components 205 such that the carrier signals 201 remain distinguishable by component amplitude. Reference is made to that copending application for further explanation.

Another method of multiplexing is phase-division multiplexing, an embodiment of which is shown in a copending application titled "PHOTOPLETHYSMOGRAPHICS USING PHASE-DIVISION MULTIPLEXING", application Ser. No. 07/665,595, Lyon & Lyon Docket No. 190/192, filed the same day in the name of the same inventors, to which reference is made for explanation of that method of multiplexing. In phase-division multiplexing, each carrier signal 201 has the same (one or more) carrier components, such that the carrier signals 201 all have the same period but are distinguishable by phase.

In a system employing phase-division multiplexing and energy-reduced carrier signals 206, the additional carrier components 205 will have no effect so long as the energy-reduced carrier signals 206 remain distinguishable by phase. In cases where the energy-reduced carrier signals 206 have a signal envelope 203 with a peak-to-trough distance 207 substantially different from 90°, it may be preferred to use a phase differential other than 90° and substantially equal to the peak-to-trough distance 207. Reference is made to that copending application for further explanation.

Error Detection and Correction

In a preferred embodiment, the additional carrier components 205 provide additional information which may be used for error detection and correction.

One preferred method of error detection and correction is majority voting. The energy-reduced carrier signals 206 each comprise a plurality of carrier components 202, so when one of that plurality is subject to noise sources (such as ambient light or electromagnetic interference) the remaining carrier components 202 may be sufficient to carry out the method of multiplexing.

In a preferred embodiment employing frequency-division multiplexing and energy-reduced carrier signals 206, each carrier signal 201 may comprise a set of three carrier components 202 w1, w2, w3. Each carrier component 202 w1, w2, w3 may be separately filtered. For each set of three carrier components 202, if any one carrier component 202 is impaired by noise, the modulation effects m1, m2 on the carrier signal may still be recovered from the remaining carrier components 202. Majority voting may be used to determine which of the three carrier components is must subject to noise. It would be clear to one of ordinary skill in the art, after perusal of the specification, drawings and claims herein, that a number of carrier components 202 other than three could be used, so long as majority voting is still possible.

In a preferred embodiment employing component-amplitude-division multiplexing and energy-reduced carrier signals 206, the additional carrier components 205 have the same error detecting and correcting effect as in the $m>n>2$ case disclosed in that copending application, to which reference is made for explanation.

In a preferred embodiment employing phase-division multiplexing and energy-reduced carrier signals 206, the additional carrier components 205 may be separately demultiplexed prior to demultiplexing of the modulation effects m1, m2 by phase. Demultiplexing by phase then produces a set of scaled copies of the data for each modulation effect m1, m2. As in the frequency-division case, majority voting may be used to determine which of the three carrier components is most subject to noise.

Alternative Embodiments

While preferred embodiments are disclosed herein, many variations are possible which remain within the concept and scope of the invention, and these variations would become clear to one of ordinary skill in the art after perusal of the specification, drawings and claims herein.

It would also be clear to one of ordinary skill in the art, after perusal of the specification, drawings and claims herein, that the invention may be adapted to measurement of other constituents, such as blood carbon dioxide, blood carbon monoxide, other blood gas concentrations, blood glucose, or more generally, other chemical and/or physical concentrations.

In a preferred embodiment, signal generation and signal manipulation as described herein are preferably performed by a digital microprocessor (such as part number DSP56001 made by Motorola) operating under software control. It would be clear to one of ordinary skill in the art, after perusal of the specification, drawings and claims herein, that programming a standard digital microprocessor to perform signal generation and signal manipulation as described herein would be a straightforward task and would not require undue experimentation.

It would also be clear to one of ordinary skill in the art, after perusal of the specification, drawings and claims herein, that the invention may be combined with known methods of computing blood oxygen concentration and other blood gas values from the modulation effects m1, m2 which are determined. Providing a system which combines the invention with such known methods would be a straightforward task, after perusal of the specification, drawings and claims herein, and would not require undue experimentation.

We claim:

1. A device for collecting photoplethysmographic data, comprising means for generating a first and a second signal, said first and second signals each comprising at least one carrier component, each said carrier component having a component energy, wherein at least one of said first and second signals has a plurality of said carrier components and has an energy less than the sum of its respective component energies;

means for applying said first and second signal to a modulating medium;

means for detecting a composite signal at an output of said modulating medium, said modulating medium having a first and a second modulating effect; and means for generating a first and a second output signal responsive to said composite signal, said first output signal corresponding to said first modulating effect applied to said first signal and said second output signal corresponding to said second modulating effect applied to said second signal.

2. A device as in claim 1, comprising means for determining, in response to a set of photoplethysmographic data, blood gas data.

3. A device as in claim 1, comprising means for determining, in response to a set of photoplethysmo-graphic data, at least one of blood oxygen, blood carbon dioxide, or blood carbon monoxide.

4. A device as in claim 1, wherein said means for generating a first and a second signal comprises means for generating first and second signals which comprise differing frequency spectra.

5. A device as in claim 1, wherein said means for generating a first and a second signal comprises means for generating first and second signals which comprise disjoint sets of carrier components.

6. A device as in claim 1, wherein said means for generating a first and a second signal comprises means for generating first and second signals which are periodic time-varying signals with differing periods.

7. A device as in claim 1, wherein said means for generating comprises means for generating first and second signals which comprise identical frequency spectra.

8. A device as in claim 1, wherein said means for generating comprises means for generating first and second signals which comprise identical sets of carrier components.

9. A device as in claim 1, wherein said means for generating comprises means for generating first and second signals which are periodic time-varying signals with identical periods.

10. A device as in claim 1, wherein said means for generating comprises means for generating first and second signals which differ in phase with respect to at least one said carrier component.

11. A device as in claim 1, wherein said means for generating comprises means for generating first and second signals which are periodic time-varying signals which are identical except for phase.

12. A device as in claim 1, wherein said means for generating comprises means for generating first and second signals which differ in amplitude for at least one carrier component.

13. A device as in claim 1, wherein said means for generating comprises means for generating first and second signals which are periodic time-varying signals which are identical except for amplitude of carrier components.

14. A device as in claim 1, wherein said means for generating a first and a second signal comprises means for generating at least one signal comprising a plurality of component signals, at least one of said carrier components comprising a sum of at least one of a sine wave or, a square wave.

15. A device as in claim 1, wherein said means for applying comprises a plurality of light-emitters.

16. A device as in claim 1, wherein said means for applying comprises a plurality of light-emitters tuned to at least two differing wavelengths.

17. A device as in claim 1, wherein said means for applying comprises means for directing at least one of said first and second signals at animal tissue.

18. A device as in claim 1, wherein said means for applying comprises means for directing at least one of said first and second signals toward at least one of blood, blood vessels, bone marrow, ligament, muscle, or skin.

19. A device as in claim 1, wherein said means for detecting comprises a photodiode.

20. A device as in claim 1, wherein said means for detecting a composite signal comprises means for detecting a sum of said first modulating effect applied to said first signal and said second modulating effect applied to said second signal.

21. A device as in claim 1, wherein said means for detecting a composite signal comprises means for detecting a composite signal comprising a result of a plurality of modulating effects, wherein at least one of said modulating effects comprises amplitude modulation.

22. A device as in claim 1, wherein said means for detecting a composite signal comprises means for detecting a composite signal comprising a result of a plurality of modulating effects, wherein said first and second modulating effects comprise an amplitude modulation effect which varies with energy wavelength.

23. A device as in claim 1, wherein said means for detecting a composite signal comprises means for detecting a composite signal comprising a result of a plurality of modulating effects, wherein at least one of said first and second modulating effects comprises a time-varying component.

24. A device as in claim 1, wherein said means for detecting a composite signal comprises means for detecting a composite signal comprising a result of a plurality of modulating effects, wherein at least one of said first and second modulating effects comprises a time-varying component which is correlated with a biological process.

25. A device as in claim 1, wherein said means for detecting a composite signal comprises means for detecting a composite signal comprising a result of a plurality of modulating effects, wherein at least one of said first and second modulating effects comprises at least one transmission response of said modulating medium at a predetermined frequency.

26. A device for collecting photoplethysmographic data, comprising
means for generating a first and a second signal, said first and second signals each comprising at least one carrier component, each said carrier component having a component energy, wherein said first signal has a plurality of said carrier components and has an energy less than the sum of its component energies;
means for applying said first and second signal to a modulating medium;
means for detecting a composite signal at an output of said modulating medium, said modulating medium having a first and a second modulating effect; and
means for generating a first and a second output signal responsive to said composite signal, said first output signal corresponding to said first modulating effect applied to said first signal and said second output signal corresponding to said second modulating effect applied to said second signal.

27. A device for collecting photoplethysmographic data, comprising
means for generating a plurality of signals, said plurality of signals each comprising at least one component signal, each said component signal having a component energy, wherein at least one of said plurality of signals has a plurality of said carrier components and has an energy less than the sum of its respective component energies;

means for applying said plurality of signals to a modulating medium;

means for detecting a composite signal at an output of said modulating medium, said modulating medium having a first and a second modulating effect; and means for generating a first and a second output signal responsive to said composite signal, said first output signal corresponding to said first modulating effect applied to said first signal and said second output signal corresponding to said second modulating effect applied to said second signal.

28. A method for collecting photoplethysmographic data, comprising the steps of generating a first and a second signal, said first and second signals each comprising at least one carrier component, each said carrier component having a component energy, wherein at least one of said first and second signals has a plurality of said carrier components and has an energy less than the sum of its respective component energies;

applying said first and second signal to a modulating medium;

detecting a composite signal at an output of said modulating medium, said modulating medium having a first and a second modulating effect; and generating a first and a second output signal responsive to said composite signal, said first output signal corresponding to said first modulating effect applied to said first signal and said second output signal corresponding to said second modulating effect applied to said second signal.

29. A method as in claim 28, comprising the step of determining, in response to a set of photoplethysmographic data, blood gas data.

30. A method as in claim 28, comprising the step of determining, in response to a set of photoplethysmographic data, at least one of blood oxygen, blood carbon dioxide, or blood carbon monoxide.

31. A method as in claim 28, wherein said step of generating said first and second signals comprises generating said first and second signals having differing frequency spectra.

32. A method as in claim 28, wherein said step of generating said first and second signals comprises generating said first and second signals having disjoint sets of carrier components.

33. A method as in claim 28, wherein said step of generating said first and second signals comprises generating said first and second signals which are periodic time-varying signals with differing periods.

34. A method as in claim 28, wherein said step of generating said first and second signals comprises generating said first and second signals which comprise identical frequency spectra.

35. A method as in claim 28, wherein said step of generating said first and second signals comprises generating said first and second signals which comprise identical sets of carrier components.

36. A method as in claim 28, wherein said step of generating said first and second signals comprises generating said first and second signals which are periodic time-varying signals with identical periods.

37. A method as in claim 28, wherein said step of generating said first and second signals comprises generating said first and second signals which differ in phase with respect to at least one said carrier component.

38. A method as in claim 28, wherein said step of generating said first and second signals comprises generating said first and second signals which are periodic time-varying signals which are identical except for phase.

39. A method as in claim 28, wherein said step of generating said first and second signals comprises generating said first and second signals which differ in amplitude for at least one carrier component.

40. A method as in claim 28, wherein said step of generating said first and second signals comprises generating said first and second signals which are periodic time-varying signals which are identical except for amplitude of carrier components.

41. A method as in claim 28, wherein said step of generating a first and a second signal comprises the step of generating at least one signal comprising a plurality of carrier components, at least one of said carrier components comprising a sum of at least one of the group: a sine wave, a square wave.

42. A method as in claim 28, wherein said step of applying comprises the step of directing at least one of said first and second signals at animal tissue.

43. A method as in claim 28, wherein said step of applying comprises the step of directing at least one of said first and second signals toward at least one of blood, blood vessels, bone marrow, ligament, muscle, or skin.

44. A method as in claim 28, wherein said step of detecting a composite signal comprises the step of detecting a composite signal which comprises a sum of said first modulating effect applied to said first signal and said second modulating effect applied to said second signal.

45. A device as in claim 28, wherein said step of detecting a composite signal comprises the step of detecting a composite signal comprising a result of a plurality of modulating effects, wherein at least one of said first and second modulating effects comprises amplitude modulation.

46. A method as in claim 28, wherein said step of detecting a composite signal comprises the step of detecting a composite signal comprising a result of a plurality of modulating effects, wherein at least one of said first and second modulating effects comprise an amplitude modulation effect which varies with energy wavelength.

47. A method as in claim 28, wherein said step of detecting a composite signal comprises the step of detecting a composite signal comprising a result of a plurality of modulating effects, wherein at least one of said first and second modulating effects comprises a time-varying component.

48. A method as in claim 28, wherein said step of detecting a composite signal comprises the step of detecting a composite signal comprising a result of a plurality of modulating effects, wherein at least one of said first and second modulating effects comprises a time-varying component which is correlated with a biological process.

49. A method as in claim 28, wherein said step of detecting a composite signal comprises the step of detecting a composite signal comprising a result of a plurality of modulating effects, wherein at least one of said first and second modulating effects comprises at least one transmission response of said modulating medium at a predetermined frequency.

50. A method for collecting photoplethysmographic data, comprising the steps of
generating a first and a second signal, said first and second signals each comprising at least one carrier component, each said carrier component having a component energy, wherein said first signal has a plurality of said carrier components and has an energy less than the sum of its component energies;
applying said first and second signal to a modulating medium;
detecting a composite signal at an output of said modulating medium, said modulating medium having a first and a second modulating effect; and
generating a first and a second output signal responsive to said composite signal, said first output signal corresponding to said first modulating effect applied to said first signal and said second output signal corresponding to said second modulating effect applied to said second signal.

51. A method for collecting photoplethysmographic data, comprising the steps of
generating a plurality of signals, said plurality of signals each comprising at least one component signal, each said component signal having a component energy, wherein at least one of said plurality of signals has a plurality of said carrier components and has an energy less than the stun of its respective component energies;
applying said plurality of signals to a modulating medium;
detecting a composite signal at an output of said modulating medium, said modulating medium having a first and a second modulating effect; and
generating a first and a second output signal responsive to said composite signal, said first output signal corresponding to said first modulating effect applied to said first signal and said second output signal corresponding to said second modulating effect applied to said second signal.

* * * * *